United States Patent [19]

Wiget

[11] Patent Number: 4,834,534
[45] Date of Patent: May 30, 1989

[54] FLOW CELL

[75] Inventor: Peter Wiget, Kussnacht, Switzerland

[73] Assignee: Kontron Holding A.G., Zurich, Switzerland

[21] Appl. No.: 188,684

[22] Filed: Apr. 21, 1988

Related U.S. Application Data

[63] Continuation of Ser. No. 21,567, Mar. 2, 1987, abandoned, which is a continuation of Ser. No. 800,242, Nov. 21, 1985, abandoned.

[30] Foreign Application Priority Data

Nov. 26, 1984 [CH] Switzerland .................. 5632/84

[51] Int. Cl.$^4$ .................. G01N 1/10; G01N 21/85
[52] U.S. Cl. .................. 356/246; 356/410
[58] Field of Search .................. 356/246, 410

[56] References Cited

U.S. PATENT DOCUMENTS 3,361,026  1/1968  Ishimaru .................. 88/14
3,751,173  8/1973  Sanz et al. .................. 356/246
3,795,450  3/1974  Munk .................. 356/246
4,440,013  4/1984  Adams .................. 356/410 X

FOREIGN PATENT DOCUMENTS 2604302  8/1976  Fed. Rep. of Germany .
8202889 10/1982  Fed. Rep. of Germany .
WO82/2596  8/1982  PCT Int'l Appl. .
1150548  4/1969  United Kingdom .

Primary Examiner—Gene Wan
Attorney, Agent, or Firm—Jon S. Saxe; Bernard S. Leon; George W. Johnston

[57] ABSTRACT

A flow cell for high performance chromatography, in which the measuring chamber is formed by a bore (12) in a plate (11) and the supply and discharge ducts are formed by bores (13, 14) in the plate (11) communicating with grooves (16, 18) in the plate surfaces (15, 17), the grooves being covered by transparent plates (19, 20) bonded on the plate surfaces, and thus forming closed ducts.

8 Claims, 2 Drawing Sheets

FLOW CELL

This application is a continuation of application Ser. No. 021,567, filed Mar. 2, 1987, now abandoned, which in turn is a continuation of Ser. No. 800,242, filed Nov. 21, 1985, now abandoned.

BACKGROUND OF THE INVENTION

1. Field of the Invention

This invention relates to a flow cell which is used, for example, in high performance chromatography.

2. Background Description

The term flow cell as used in this specification denotes devices for measuring the optical properties of continuously flowing liquids. These devices basically comprise an inner chamber defined on opposite sides by optical windows, and in which a liquid, that is supplied and discharged by suitable connections, is subjected to a radiation (e.g. light) for measuring purposes. There are numerous proposals for using such flow cells in various applications.

In high performance chromatography, the flow cells used in detectors—normally fluorescence or absorption measuring devices—must satisfy extreme requirements. They must withstand high pressures of up to 400 bars, have high thermal resistance, be resistant to aggressive or corrosive solvents, be fully transparent in the ultraviolet and visible range and have minimum dead volume.

One of the main problems hitherto was the seals or gaskets, which usually consist of polytetrafluoroethylene, known by the name Teflon, a material which although it extensively satisfies certain of these requirements does not do so completely. In particular, the space alongside the seal including the liquid creeping between seal and solid surfaces forms dead volumes which result in remixing and must therefore be negligibly small in relation to the cell volume to avoid incorrect readings. Their existence limits the minimum value of possible cell volumes. The problem of dead volume hitherto was not solved in the optimum way.

If the cell were made of a material such as metal having low thermal resistance, there is an additional problem that thermal instability between the pulsating liquid and the metal cell walls gives rise to refractive index fluctuations which finally result in interfering fluctuations (noise) of the measurement signal.

SUMMARY OF THE INVENTION

This invention provides a flow cell which satisfies the above requirements and, in particular, has much smaller dead volumes than known flow cells.

This problem is solved according to the invention by a flow cell having the features of the claims.

With the present invention, the flow cell has a measuring chamber bounded by optical windows on opposite sides, and has connecting ducts with external connections for the supply and discharge of the liquid being measured. The measuring chamber is defined by a bore in an inner plate having plane-ground and polished surfaces, and two outer plates are bonded to the inner plate on both sides. The connecting ducts are formed at least partially by grooves in the polished surfaces of the inner plate, which grooves are covered by the outer plates. The inner and outer plates consists of a bondable material and the outer plates are transparent.

BRIEF DESCRIPTION OF THE DRAWINGS

Preferred embodiments of the invention are described hereinafter with reference to the accompanying drawings wherein.

DETAILED DESCRIPTION OF THE PREFERRED EMBODIMENTS

The present invention concerns flow cells used, for example, in high performance chromatography for measuring the optical properties of continuously flowing liquids.

In accordance with the invention, the flow cell comprising a measuring chamber having an inner plate and two transparent outer plates. The inner plate has plane-ground and polished opposing surfaces, a bore passing through it from one polished surface to the other and a groove in each surface. The two outer plates each have a plane-ground and polished surface secured respectively to the polished surfaces of the inner plate and cover the grooves in the inner plate so as to form ducts. External connections communicate with the ducts for supplying and discharging liquid to the measuring chamber. Optical windows are secured on opposite sides of the measuring chamber.

In another preferred embodiment, the outer plate which receives light for the measuring of the optical properties of the liquid has a ground, inclined surface located and configured to deflect a portion of the light.

Figure 1:
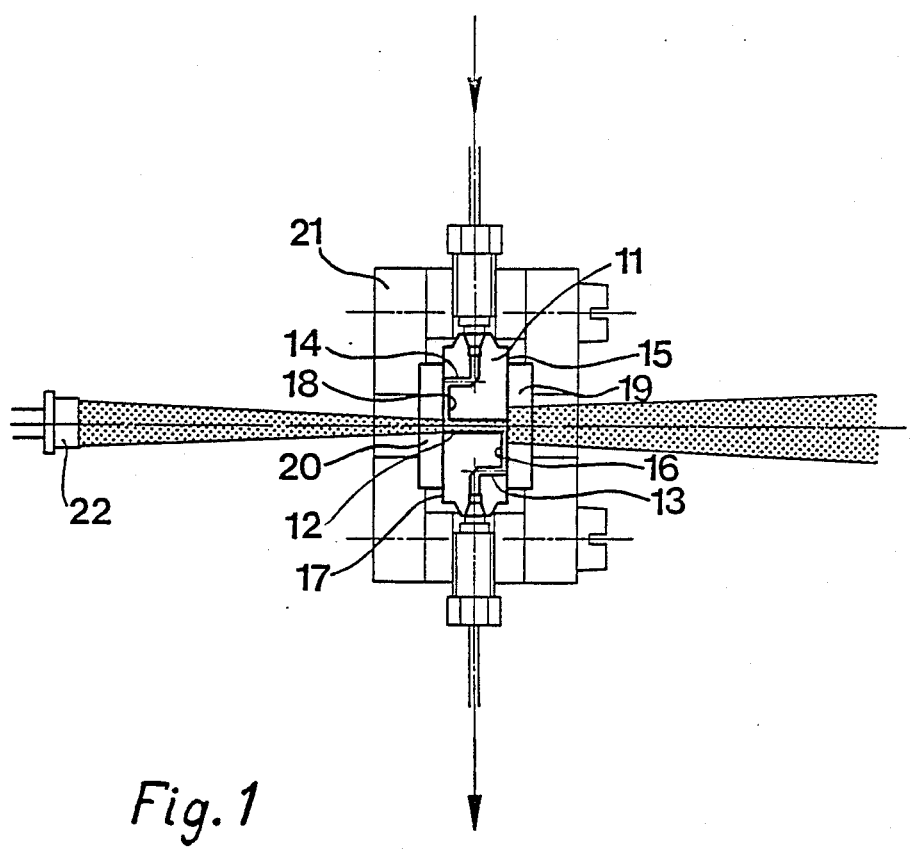
FIG. 1 is a diagram showing a flow cell for an apparatus for high-performance chromatography in accordance with the invention.
Figure 2:
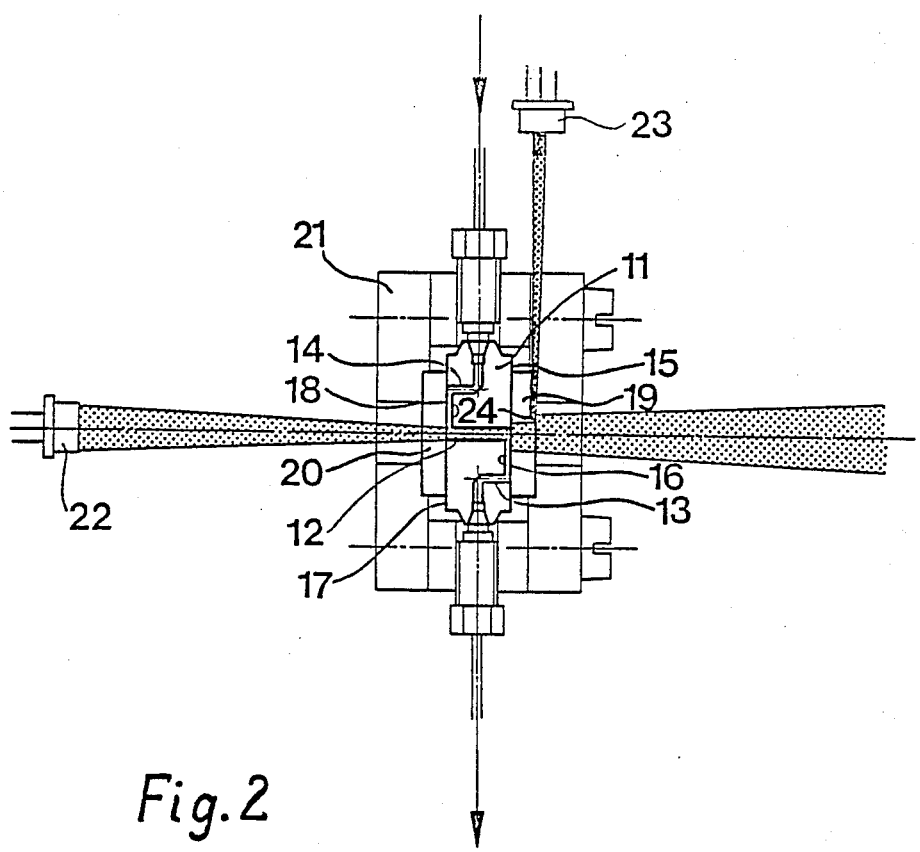
FIG. 2 is another embodiment of the inventive flow cell.

With reference to FIGS. 1 and 2, an inner plate 11 has a central continuous bore 12 which represents the measuring volume of the measuring chamber of the flow cell. The length of the bore 12 is equal to the plate thickness and represents the thickness of the film of the liquid sample under measurement.

A second bore 13 bent at 90° extends from one plate surface 15 initially parallel to the central bore 12 and then perpendicularly thereto to one end face of the inner plate 11. At the same distance from the central bore 12 to the other side there extends another bent-off bore 14 from the second plate surface 17 to the opposite end face.

A groove 16 extends in one plate surface 15 between the central bore 12 and the one lateral bore 13, while in the other plate 17 a similar groove 18 extends between the central bore 12 and the other lateral bore 14.

The plate surfaces 15 and 17 are plane-ground and polished.

One plate surface 15 adjoins a likewise plane-ground and polished surface of outer plate 19 which is smaller than the inner plate 11 but which covers that zone of the plate surface 15 in which the groove 16 extends.

The other surface 17 of the inner plate 11 adjoins an outer plate 20 of the same type and arrangement. The two outer plates 19, 20 with the grooves 16 and 18 form closed ducts. With the three bores, they thus together form a S-shaped duct through which the medium under analysis flows. For the connection to the supply and discharge conduits, the two outer bores 13, 14 are so drilled open where they meet the end faces of the plate as to enable tubes with ferrule seals to be inserted (not shown).

A particularly important feature of the invention is that no seal is now required between the inner plates 11 and outer plates 19 or 20. To this end, the surfaces 15 and 17, and the adjacent surfaces of the plates 19 and 20, must be ground and polished to be so plane and smooth as to adhere to one another by the bonding effect known from the manufacture of optical lenses, so that they can be separated only by the application of considerable force. Plates bonded in this way have no air gap between them and are therefore sealing-tight to liquids. Applications with high liquid pressure (>50 bars) are also possible without difficulty, although in these cases the outer two plates 19, 20 must be pressed against the middle plate 11 by mechanical biasing.

It is well known that it is an easy matter to slide laterally in relation to one another surfaces which are bonded together in this way. To secure the plates 11, 19, 20 against lateral sliding, for providing the connections, and for pressing together at higher internal pressure, a mounting 21 is provided in which the plates are held under a certain tension by a screw connection or the like.

The path of the light used during the measuring of the optical properties of the liquid extends parallel to the axis of the middle bore 12 through the plates 19 and 20 (right to left with reference to FIGS. 1 and 2). The plates 19 and 20 must therefore be transparent, e.g. be made for example from glass, quartz, sapphire etc. The plate 11 may be made from the same material or an opaque material, e.g. ceramics. In any case, the material must be such as to enable its surface to be machined to the quality required for bonding. This is not the case with most materials, particularly most metals.

Bores concentric with the middle bore 13 are provided in the plates of mounting 21 for the passage of the rays.

In operation of this cell the liquid to be optically measured flows in the direction indicated by the arrows. Due to the absence of seals there are no dead volumes to cause remixing. Accordingly, cell volumes can be employed which are much smaller than those known before.

FIG. 2 shows an embodiment of substantially the same construction as the previously described flow cell of FIG. 1. Unlike the latter, however, the plate 19 has a ground, inclined surface 24 in the path of the light beam rays on the light entry side. Part of the beam is thus deflected to a reference detector 23, while the remaining part continues to reference detector 22.

I claim:

1. A flow cell for measuring the optical properties of a liquid, comprising a measuring chamber bounded by optical windows on opposite sides of the measuring chamber, and having connecting ducts with external connections for the supply and discharge of a liquid being measured, the measuring chamber being defined by a bore in an inner plate having plane-ground and polished surfaces and transparent outer plates forming said optical windows, said outer plates having plane-ground and polished surfaces which are bonded to the polished surfaces of the inner plate, said plate surfaces ground and polished to a predetermined degree so as to adhere to each other without applying external pressure, and the connecting ducts being formed at least partially of grooves in the surfaces of the inner plate, said grooves being covered by the outer plates to form said connecting ducts, the plates being made of a bondable material.

2. The flow cell of claim 1, that wherein the inner or outer plate is glass, quartz or sapphire.

3. The flow cell of claim 1, wherein the inner plate is a ceramic.

4. The flow cell of claim 1, wherein the outer plate which is situated on the light entry side of the measuring chamber has a plane-ground, inclined surface by means of which part of the light is deflected.

5. The flow cell of claim 1 wherein the ducts and bore form a generally S-shaped conduit through which the liquid flows.

6. A flow cell for measuring the optical properties of a flowing liquid comprising:
   (a) a measuring chamber having:
      (i) an inner plate with plane-ground and polished opposing surfaces, a bore passing through the inner plate from one polished surface to the other, and a groove in each surface; and
      (ii) two transparent, outer plates which serve as optical windows each having a plane-ground and polished surface secured respectively to the polished surfaces of the inner plate and covering said grooves to form ducts, said plate surfaces ground and polished to a predetermined degree so as to adhere to each other without applying external pressure; and
   (b) external connections communicating with the ducts for supplying and discharging the liquid to the measuring chamber.

7. The flow cell of claim 6, wherein one of the outer plates has a plane-ground, inclined surface located and configured to deflect a portion of a light beam used in measuring the optical properties of the liquid.

8. The flow cell of claim 6 wherein the ducts and bore from a generally S-shaped conduit through which the liquid flows.

* * * * *